United States Patent [19]

Kudoh et al.

[11] Patent Number: 4,916,236

[45] Date of Patent: Apr. 10, 1990

[54] PREPARATION OF INDOLES BY CYCLIZATION

[75] Inventors: Akihide Kudoh, Yokohama; Tadatoshi Honda, Hiratsuka; Makoto Kotani; Kazuhiro Terada, both of Yokohama; Takeshi Tsuda, Kouza; Shinji Kiyono, Yokohama, all of Japan

[73] Assignee: Mitsui Toatsu Chemicals, Inc., Tokyo, Japan

[21] Appl. No.: 270,067

[22] Filed: Nov. 14, 1988

Related U.S. Application Data

[63] Continuation of Ser. No. 930,188, Nov. 13, 1986, abandoned, which is a continuation of Ser. No. 752,543, Jul. 8, 1985, abandoned, which is a continuation of Ser. No. 508,011, Jun. 27, 1983, abandoned.

[30] Foreign Application Priority Data

Jul. 8, 1982 [JP]  Japan ................................. 57-117824

[51] Int. Cl.$^4$ ..................... C07D 209/08; C07B 37/10
[52] U.S. Cl. ..................................................... 548/508
[58] Field of Search ........................................ 548/508

[56]             References Cited

U.S. PATENT DOCUMENTS 4,376,205  3/1983  Matsuda et al. ..................... 548/508
4,436,916  4/1984  Matsuda et al. ..................... 548/508
4,443,615  4/1984  Matsuoka et al. ................... 548/508

FOREIGN PATENT DOCUMENTS 55-108850  8/1980  Japan ................................... 548/508
56-005459  1/1981  Japan ................................... 548/508
56-113761  9/1981  Japan ................................... 548/508
57-035564  2/1982  Japan ................................... 548/508

OTHER PUBLICATIONS

Article by Takaoka, Accetone, Methyl Ethyl Ketone and Methyl Isobutyl Ketone of May, 1972, Process Economics Program, Stanford Research Institute, Menlo Park, CA.
Article, The Oil and Gas Journal, Jun. 15, 1981, p. 153.
The Encyclopedia of Chemical Technology, vol. 19, p. 64.
MTC-I Chemical Abstracts, 95, 115293b.
MTC-II Chemical Abstracts, 95, 115295d.

*Primary Examiner*—Mark L. Berch
*Attorney, Agent, or Firm*—Fisher, Christen & Sabol

[57]             ABSTRACT

Disclosed herein is a preparation process for an indole, which process comprises subjecting an N-($\beta$-hydroxy)-alkylaniline, in the presence of a catalyst and at a superatmospheric pressure, to a gas-phase catalytic reaction. The present process improves the selectivity of the reaction and the service life of the catalyst.

7 Claims, 1 Drawing Sheet

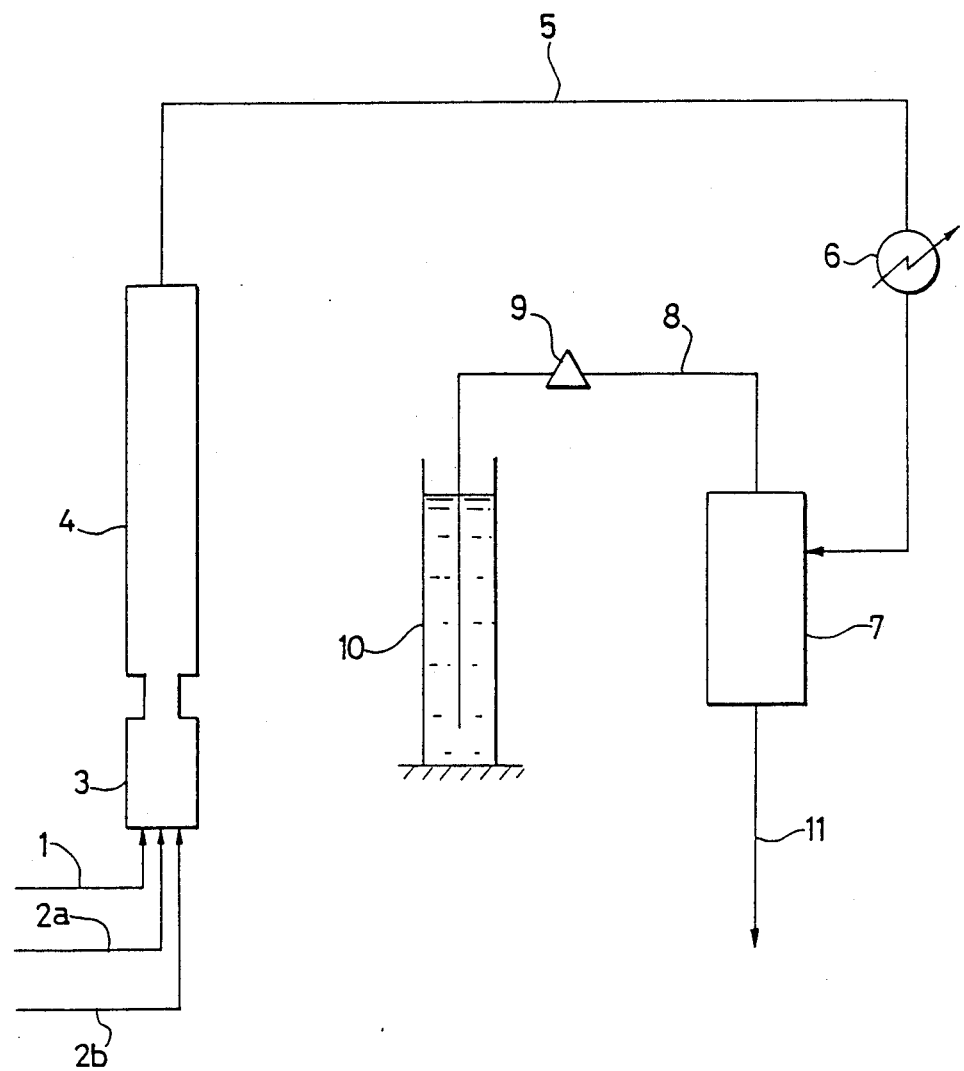

PREPARATION OF INDOLES BY CYCLIZATION

This is a continuation of application Ser. No. 930,188, filed on Nov. 13, 1986, now abandoned which is a continuation of application Ser. No. 752,543, filed on July 8, 1985, now abandoned, which is a continuation of application Ser. No. 508,011, filed on June 27, 1983, now abandoned.

BACKGROUND OF THE INVENTION (1) Field of the Invention

This invention relates to an improved process for preparation of indoles using N-($\beta$-hydroxy)alkylanilines as their raw materials.

(2) Description of the Prior Art

Indoles have been known as raw materials for the chemical industry and the importance of indole in particular has increased in recent years as raw materials for the syntheses of fragrant substances and amino acids.

A number of attempts have heretofore been made with a view toward synthetically obtaining indoles. However, these attempts were all accompanied by one or more of such problems as multiple step preparation processes being necessary, many by-products being produced, etc.

Among such prior art processes, the preparation process of indoles relying upon gas-phase catalytic reactions of N-($\beta$-hydroxy)alkylanilines needed a further improvement in terms of its selectivity and was accompanied by such problems as severe activity reduction of catalysts due to accumulation of carbonaceous deposits on their surfaces.

SUMMARY OF THE INVENTION

An object of this invention is to provide a process for preparing an indole through a gas-phase reaction of an N-($\beta$-hydroxy)alkylaniline while suppressing the activity reduction of the catalyst and assuring an improved selectivity for the indole.

To achieve the above object, the present inventors engaged in a detailed study of gas-phase catalytic reactions of N-($\beta$-hydroxy)alkylanilines. As a result, it has surprisingly been found, contrary to the Le Chatelier-Braun's principle, that it is possible not only to suppress the activity reduction of the catalyst but also to improve the selectivity for the formation of the intended indole by carrying out the reaction at a superatmospheric pressure.

This invention therefore provides the following preparation process for indoles:

In a process for preparing an indole by subjecting an N-($\beta$-hydroxy)alkylaniline to a gas-phase catalytic reaction in the presence of a catalyst, the improvement which comprises that the reaction is carried out at a superatmospheric pressure.

In the present invention, for example, N-($\beta$-hydroxy)ethylaniline undergoes a reaction in accordance with the following chemical equation:

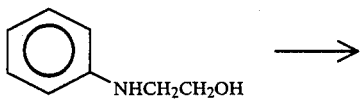

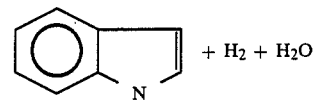

BRIEF DESCRIPTION OF THE DRAWING

In the drawing, the single figure is a simplified flow diagram showing the outline of the arrangement of reaction facilities used in Example 1.

DETAILED DESCRIPTION OF THE INVENTION

N-($\beta$-hydroxy)alkylanilines useful in the practice of the process according to this invention may be represented by the following general formula (I):

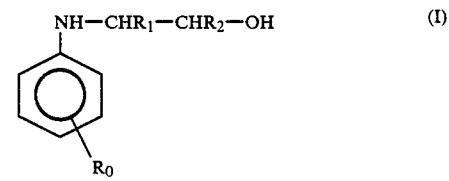

wherein $R_0$ and $R_1$ mean individually a hydrogen or halogen atom or a hydroxyl, unsubstituted alkyl, substituted alkyl or alkoxy group and $R_2$ denotes a hydrogen or halogen atom or an unsubstituted alkyl, substituted alkyl or alkoxy group, with a proviso that the 2nd or 6th position relative to the substituted amino group is unsubstituted by $R_0$.

In the above general formula (I), $R_0$ may preferably be a hydrogen or halogen atom or a hydroxyl, unsubstituted alkyl or alkoxy group and $R_1$ and $R_2$ may preferably and individually be a hydrogen or halogen atom or an alkyl group which may optionally be substituted. More preferably, $R_0$ may be a hydrogen or halogen atom or a hydroxyl, methyl or methoxy group and $R_1$ and $R_2$ may individually be a hydrogen atom or a methyl, ethyl or $\beta$-hydroxyethyl group. As more specific exemplary N-($\beta$-hydroxy)alkylanilines, may be mentioned:

N-($\beta$-hydroxy)ethylaniline;
N-($\beta$-hydroxy)ethyltoluidines;
N-($\beta$-hydroxy)ethylhaloanilines;
N-($\beta$-hydroxy)ethylhydroxyanilines;
N-($\beta$-hydroxy)ethylanisidines;
N-($\alpha$-alkyl-$\beta$-hydroxy)ethylanilines;
N-($\alpha$-alkyl-$\beta$-hydroxy)ethyltoluidines;
N-($\alpha$-alkyl-$\beta$-hydroxy)ethylhaloanilines;
N-($\alpha$-alkyl-$\beta$-hydroxy)ethylhydroxyanilines;
N-($\alpha$-alkyl-$\beta$-hydroxy)ethylanisidines;
N-($\alpha$-halo-$\beta$-hydroxy)ethylanilines;
N-($\alpha$-halo-$\beta$-hydroxy)ethylhaloanilines;
N-($\alpha$-halo-$\beta$-hydroxy)ethylhydroxyanilines;
N-($\alpha$-halo-$\beta$-hydroxy)ethylanisidines;
N-($\alpha$-alkyl-$\beta$-hydroxy)ethylanilines;
N-($\alpha$-alkyl-$\beta$-hydroxy)ethyltoluidines;
N-($\beta$-alkyl-$\beta$-hydroxy)ethylhaloanilines;
N-($\beta$-alkyl-$\beta$-hydroxy)ethylhydroxyanilines;
N-($\beta$-alkyl-$\beta$-hydroxy)ethylanisidines;
N-($\beta$-halo-$\beta$-hydroxy)ethylanilines;
N-($\beta$-halo-$\beta$-hydroxy)ethylhaloanilines;
N-($\beta$-halo-$\beta$-hydroxy)ethylhydroxyanilines;
N-($\beta$-halo-$\beta$-hydroxy)ethylanisidines; etc.

The following catalysts may be employed in the practice of the process according to this invention:

(1) Catalysts containing the oxide or hydroxide of at least one element selected from the group consisting of Si, Al, B, Sb, Bi, Sn, Pb, Ga, Ti, In, Sr, Ca, Zr, Be, Mg, Y, Cu, Ag, Zn, Cd and the lanthanides (hereinafter called "catalyst material (1)"), including, for example, CdO, $Al_2O_3$-$B_2O_3$, $SiO_2$-ZnO, $SiO_2$-CaO, $SiO_2$-$In_2O_3$, $SiO_2$-SrO, $SiO_2$-CdO, $SiO_2$-MgO, $TiO_2$-$SnO_2$, CdO-$Bi_2O_3$, $SiO_2$-$Y_2O_3$, $SiO_2$, $Bi_2O_3$-$B_2O_3$, $SiO_2$-$La_2O_3$, $SiO_2$-$Ce_2O_3$, $SiO_2$-ZnO-AgO, $SiO_2$-MgO-CuO, etc.;

(2) Catalysts containing the sulfide or selenide of at least one element selected from the group consisting of Pd, Pt, Cr, Fe, Ni, Co, Zn, Mo, Cd and W (hereinafter called "catalyst materials (2)"), including, for example, PdS, PtS, CrS, FeS, NiS, CoS, ZnS, $MoS_2$, CdS, $WS_2$, ZnSe, CdSe, etc.;

(3) Catalysts containing an inorganic salt, namely, a halide, carbonate, sulfate, phosphate, pyrophosphate, phosphomolybdate or silicotungstate of Fe, Tl, Ca, Mn, Bi, Sr, Y, Al, Zn, Cd, Ni, Mg, In, Be, Co, Ga and the lanthanides (hereinafter called "catalyst materials (3)"), including, for example, ferric sulfate, thallium sulfate, calcium sulfate, manganese sulfate, bismuth sulfate, strontium sulfate, yttrium sulfate, cadmium bromide, aluminum sulfate, zinc sulfate, nickel sulfate, cadmium chloride, magnesium sulfate, indium sulfate, beryllium sulfate, cobalt sulfate, zinc aluminum sulfate, magnesium chloride, cadmium sulfate, cadmium phosphate, etc.; and (4) Metallic catalysts containing at least one element selected from the group consisting of Cu, Ag, Pt, Pd, Ni, Co, Fe, Ir, Os, Ru and Rh (hereinafter called "catalyst materials (4)").

These catalysts may be prepared in any manner known in the art. Namely, the catalyst materials (1) may be prepared by hydrolyzing water-soluble salts of catalyst-constituting elements into their hydroxides and then drying and calcining the thus-obtained gels or by subjecting readily-decomposable salts of catalyst-constituting elements to thermal decomposition in air.

The catalyst materials (2) may be prepared by adding sodium sulfide or potassium selenide to water-soluble salts of catalyst-constituting elements or bringing catalyst-constituting elements or their salts into contact with hydrogen sulfide gas or hydrogen selenide gas.

The catalyst materials (4) may be prepared by reducing salts, hydroxides or oxides of catalyst-constituting elements with a reducing agent such as hydrogen, formaldehyde, formic acid, phosphorous acid, hydrazine or the like.

These catalysts may contain the above-described catalyst materials (1), (2), (3) and (4) either singly or in combination as mixtures. Such catalyst materials may also be carried on carriers. Any conventionally-used carriers may be used but it is common to use diatomaceous earth, pumice, titania, silica-alumina, alumina, magnesia, silica gel, activated carbon, activated clay, asbestos or the like. Carrier-supported catalysts are prepared by causing these carriers to support the above-described catalyst materials in a manner commonly known in the art.

There is no particular limitation to the amount of each of the above catalyst materials to be supported on a carrier. Each of the above catalyst materials may normally be carried in a suitable amount, for example, 1–50% depending on the type of a carrier to be used.

As catalysts which may preferably be usable in the process according to this invention, may be mentioned catalysts containing zinc sulfide, cadmium sulfide, magnesium chloride, cadmium sulfate, zinc sulfate, aluminum sulfate, zinc, platinum, palladium or ruthenium as well as catalysts containing copper or silver as the metal or oxide.

The particularly preferred catalyst for the practice of the process according to this invention is a catalyst which contains Cu or Ag as the metal or oxide in an amount of 1–50 wt. % or preferably 5–50 wt. % and $SiO_2$ in an amount of 10 wt. % or more.

The reaction of the process according to this invention is conducted in the presence of the above-described catalyst and in a gas phase. The reaction may be effected in any of a fixed bed reactor, fluidized bed reactor or moving bed reactor.

The N-($\beta$-hydroxy)alkylaniline, which is the raw material for the reaction, may be charged at a feed rate in the range of 0.005–10 $hr^{-1}$, particularly 0.01–10 $hu^{-1}$, in terms of liquid hourly space velocity. It may be charged into the reactor after vaporizing in an evaporator in advance. Here, it is feasible to feed, together with the thus-vaporized raw material, aniline, steam, hydrogen, carbon monoxide, methane, benzene, toluene, nitrogen, neon, argon or the like as a carrier gas. Among these carrier gases, use of aniline and use of steam or hydrogen are particularly preferred because aniline is effective in improving the yield of the intended reaction product while steam or hydrogen is effective in prolonging the regeneration cycle of the catalyst.

The reaction temperature may range from 200° to 600° C. or, preferably, from 250° to 500° C.

The term "a superatmospheric pressure" as used herein means a pressure which is above the standard atmospheric pressure and does not permit any of various components present in the reaction zone to form a condensate phase. Practically speaking, the superatmospheric pressure may preferably range from $1.1 \times 10^5$ Pa to $5.0 \times 10^6$ Pa and, more preferably, from $2.0 \times 10^5$ Pa to $3.0 \times 10^6$ Pa. When a carrier gas is fed together with the raw material, the total reaction pressure is the sum of the partial pressure of the raw material and the partial pressure of the carrier gas.

Generally speaking, it is preferable to raise the reaction pressure where the reaction temperature is high and to lower the reaction pressure where the reaction temperature is low. It is preferable to limit the partial pressure of hydrogen below $1.0 \times 10^6$ Pa when using a catalyst containing a material having high hydrogen-activating capacity and using hydrogen as a carrier gas.

The process according to this invention is effective in suppressing the activity reduction of each catalyst, although causes for the above effect of the present invention has not been fully elucidated.

The invention will be described in the following Examples:

EXAMPLE 1 AND COMPARATIVE EXAMPLE 1:

An experiment was carried out using the autoclave illustrated in the figure. Packed in a cylindrical reactor 4 made of stainless steel and having the internal diameter of 20 mm were 400 cc of a pellet-like catalyst each 3 mm in diameter and 2.5 mm in height, which catalyst had been obtained by tabletting commercial cadmium sulfide. A 1:5 mixture in terms of molar ratio of N-($\beta$-hydroxy)ethylaniline and aniline and water were respectively charged through a feed line 1 and a feed line 2b and at 80 g/hr and 20 g/hr into the evaporator 3 while maintaining each of the evaporator 3 and the cylindrical reactor 4 at the internal temperature of 340° C. At the same time, hydrogen gas was also charged through a feed line 2a at 50 l/hr as measured under standard conditions. The effluent stream was guided from the reactor 4, through a line 5 and into a condenser 6, where it was cooled. The resultant liquid condensate was separated from the gas phase in a gas-liquid separator 7 and discharged through a line 11. On the other hand, the gas phase was delivered through a line 8, depressurized while passing through a reducing valve 9, and discharged through a water-sealed cylinder 10.

The synthesis reaction of indole was conducted by changing the total reaction pressure as follows. Results are shown in Table 1.

TABLE 1

| | Reaction Pressure (Pa) | Reaction results | Reaction time (hr) 50 | 100 |
|---|---|---|---|---|
| Ex. 1 | $8.0 \times 10^5$ | Conversion of N-($\beta$-hydroxy)-ethylaniline (%) | 94 | 91 |
| | | Selectivity of indole (%) | 72 | 73 |
| Comp. Ex. 1 | $1.0 \times 10^5$ | Conversion of N-($\beta$-hydroxy)-ethylaniline (%) | 83 | 75 |
| | | Selectivity of indole (%) | 65 | 67 |

EXAMPLES 2–3 AND COMPARATIVE EXAMPLES 2–3:

Following the procedure of Example 1, the reaction was carried out by changing the catalyst only. In the Comparative Examples, the reactions were carried out at normal pressure. Results are summarized in Table 2.

EXAMPLE 4 COMPARATIVE EXAMPLE 4:

Water glass, copper nitrate, zinc nitrate and an aqueous solution of manganese nitrate were mixed and then treated in accordance with the coprecipitation method, i.e., neutralized with an aqueous ammonia solution, thereby obtaining a precipitate containing Cu, Si, Zn and Mn at the weight ratio of 40 : 20 : 30 : 10 as measured as their oxides (CuO : SiO$_2$ ZnO : MnO). After washing the precipitate thoroughly with water, it was dried at 110° C. for 3 hours, ground, tabletted, and then fired at 500° C. for 3 hours. Using the thus-obtained catalyst, experiments were carried out in the same manner as in Example 1. In the Comparative Example, the reaction was conducted at normal pressure. Results are shown in Table 2.

EXAMPLES 5–8 COMPARATIVE EXAMPLES 5–8:

Following the procedure of Example 4, there was prepared a catalyst having the composition given in Table 2. Reactions were carried out in the same manner as in Example 1. In the Comparative Examples, the reactions were carried out at normal pressure. Results are given in Table 2.

EXAMPLE 9 AND COMPARATIVE EXAMPLE 9:

Following the procedure of Example 4, there was prepared a carrier having the composition given by weight ratio in Table 2. The thus-obtained carrier was immersed in an aqueous solution which contained 5 moles/liter of ammonia and 0.1 mole/liter of silver acetate, dried, immersed in a 3% aqueous solution of hydrazine, and then dried. This immersion and drying procedures were repeated, thereby preparing a catalyst carrying 10 wt. % of Ag. Reactions were conducted in the same manner as in Example 1. In the Comparative Example, the reaction was carried out at normal pressure. Results are shown in Table 2.

EXAMPLES 10–13 COMPARATIVE EXAMPLES 10–12:

Following the procedure of Example 9, there was prepared a Cu or Ag catalyst carried on a carrier having the composition given in Table 2. Reactions were carried out in the same manner as in Example 1. In the Comparative Examples, the reactions were carried out at normal pressure. Results are given in Table 2.

TABLE 2

| | Reaction pressure ($\times 10^5$ Pa) | Catalyst | Reaction results (%) | Reaction time (hr) 50 | 100 |
|---|---|---|---|---|---|
| Ex. 2 | 6.0 | Cu—Cr Catalyst ("C-43", product of Catalysts & Chemicals Inc., Far East) | NHEA-C* I-S** | 97 64 | 91 58 |
| Ex. 3 | 8.0 | Pt/SiO$_2$ Catalyst (7 wt. % Pt carried) | NHEA-C I-S | 96 58 | 90 61 |
| Ex. 4 | 6.0 | CuO—SiO$_2$—ZnO—MnO (40-20-30-10) | NHEA-C I-S | 98 69 | 96 67 |
| Ex. 5 | 5.0 | CuO—SiO$_2$—ZnO—MgO (30-50-5-15) | NHEA-C I-S | 97 66 | 94 68 |
| Ex. 6 | 8.0 | AgO-SiO$_2$—ZnO (30-50-20) | NHEA-C I-S | 98 63 | 95 65 |
| Ex. 7 | 8.0 | CuO—SiO$_2$—MgO (30-50-20) | NHEA-C I-S | 98 67 | 95 69 |
| Ex. 8 | 8.0 | CuO—SiO$_2$ (33-67) | NHEA-C I-S | 94 61 | 92 58 |
| Ex. 9 | 8.0 | Ag/SiO$_2$—ZnO (Ag 10 wt. %/90-10) | NHEA-C I-S | 97 77 | 95 77 |
| Ex. 10 | 6.0 | Cu/SiO$_2$—ZnO—CaO (Cu 10 wt. %/81-14-5) | NHEA-C I-S | 98 73 | 96 74 |
| Ex. 11 | 8.0 | Ag/SiO$_2$—In$_2$O$_3$ (Ag 10 wt. %/90-10) | NHEA-C I-S | 95 76 | 93 77 |
| Ex. 12 | 6.0 | Cu/SiO$_2$—GeO$_2$ (Cu 10 wt. %/90-10) | NHEA-C I-S | 97 70 | 96 71 |
| Ex. 13 | 30.0 | Cu/SiO$_2$-GeO$_2$ (Cu 10 wt. %/95-5) | NHEA-C I-S | 96 68 | 92 68 |
| Comp. | 1.0 | The same catalyst as | NHEA-C | 68 | 50 |

TABLE 2-continued

| | Reaction pressure ($\times 10^5$ Pa) | Catalyst | Reaction results (%) | Reaction time (hr) 50 | 100 |
|---|---|---|---|---|---|
| Ex. 2 | | used in Ex. 2 | I-S | 57 | 48 |
| Comp. Ex. 3 | 1.0 | The same catalyst as used in Ex. 3 | NHEA-C I-S | 93 35 | 89 36 |
| Comp. Ex. 4 | 1.0 | The same catalyst as used in Ex. 4 | NHEA-C I-S | 87 59 | 76 52 |
| Comp. Ex. 5 | 1.0 | The same catalyst as used in Ex. 5 | NHEA-C I-S | 83 58 | 73 50 |
| Comp. Ex. 6 | 1.0 | The same catalyst as used in Ex. 6 | NHEA-C I-S | 84 56 | 72 51 |
| Comp. Ex. 7 | 1.0 | The same catalyst as used in Ex. 7 | NHEA-C I-S | 83 57 | 74 54 |
| Comp. Ex. 8 | 1.0 | The same catalyst as used in Ex. 8 | NHEA-C I-S | 78 55 | 69 51 |
| Comp. Ex. 9 | 1.0 | The same catalyst as used in Ex. 9 | NHEA-C I-S | 82 56 | 73 57 |
| Comp. Ex. 10 | 1.0 | The same catalyst as used in Ex. 10 | NHEA-C I-S | 79 52 | 68 50 |
| Comp. Ex. 11 | 1.0 | The same catalyst as used in Ex. 11 | NHEA-C I-S | 83 58 | 72 55 |
| Comp. Ex. 12 | 1.0 | The same catalyst as used in Ex. 12 | NHEA-C I-S | 85 54 | 76 53 |

Note:
*NHEA-C: Conversion (%) of N-(β-hydroxy)ethylaniline.
**I-S: Selectivity of indole.

What is claimed is:

1. A process for preparing indole comprising contacting a vaporous mixture of N-(β-hydroxy) ethylaniline, aniline, water and hydrogen with a catalyst selected from the group consisting of a cadmium sulfide catalyst, a copper-chromium catalyst, a catalyst of platinum carried on silica, a catalyst of silver carried on $SiO_2$-ZnO, a catalyst of silver carried on $SiO_2$-$In_2O_3$ an AgO-$SiO_2$-ZnO catalyst, a catalyst of copper carried on $SiO_2$-ZnO-CaO, a catalyst of copper carried on $SiO_2$-ZnO-CaO, a catalyst of copper carried on $SiO_2$-$GeO_2$, a CuO-SiO catalyst, a CuO-SiO-MgO catalyst, a CuO-SiO-ZnO-MnO catalyst, a CuO-MgO-MnO-SiO catalyst and a CuO-SiO-ZnO-MgO catalyst, at a temperature of 200° to 600° and at a liquid hourly space velocity of the N-(β-hydroxy) ethylaniline of 0.01 to 10 hr$^{-1}$, and cooling the resulting vaporous reaction mixture containing indole to condense the indole, wherein the improvement comprises conducting the reaction at a presence ranging from $2.0 \times 10^5$ Pa to $3.0 \times 10^6$ Pa such that said vaporous mixture does not form a condensate and the catalyst is not substantially deactivated after a duration of about 100 hours of said contacting step.

2. The process as claimed in claim 1 wherein the compound of the formula (I) is N-(β-hydroxy)ethylaniline.

3. The process as claimed in claim 2 wherein the N-(β-hydroxy)alkylanilin is charged at a feed rate in the range 0.005 to 10 hr$^{-1}$ in terms of liquid hourly space velocity.

4. The process as claimed in claim 3 wherein the N-(β-hydroxy)alkylanilin is vaporized and then fed to a reaction zone together with a carrier gas selected from the group consisting of aniline, steam, hydrogen, carbon monoxide, methane, benzene, toluene, nitrogen, neon and argon.

5. The process as claimed in claim 4 wherein the carrier gas is aniline.

6. The process as claimed in claim 1 wherein the catalyst contains copper, silver, copper oxide or silver oxide in an amount of 1 to 50 wt. percent and silicon dioxide in an amount of at least 10 wt. percent, and wherein the N-(β-hydroxy) alkylaniline is vaporized and then fed to a reaction zone together with aniline, a carrier gas.

7. A process for preparing an indole comprising contacting the vapor of an N-(β-hydroxy) alkylaniline as represented by the following formula (1):

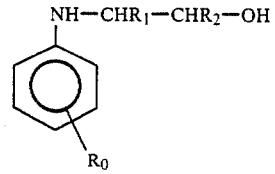

wherein $R_0$ is a hydrogen or halogen atom or a hydroxyl, methyl or methoxy group, and $R_1$ and $R_2$ are individually a hydrogen atom or methyl, ethyl or β-hydroxyethyl group with a catalyst containing at least one member selected from the group consisting of copper, silver, zinc, copper oxide, silver oxide, zinc sulfide, cadmium sulfide, magnesium chloride, cadmium sulfate, zinc sulfate and aluminum sulfate at a temperature of 200° to 600° C. exclusively in the vapor phase to form the indole, and recovering the indole from the resulting vaporous reaction mixture by condensation, wherein the improvement comprises conducting the reaction at a superatmospheric pressure ranging from $2.0 \times 10^5$ Pa to $3.0 \times 10^6$ Pa.

* * * * *